United States Patent
Deshmukh et al.

(10) Patent No.: US 6,919,471 B2
(45) Date of Patent: Jul. 19, 2005

(54) PROCESS FOR PREPARING ALKYL/ARYL CHLOROFORMATES

(75) Inventors: Abdul Rakeeb Abdul Subhan Deshmukh, Maharashtra (IN); Vikas Kalyanrao Gumaste, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/665,410

(22) Filed: Sep. 22, 2003

(65) Prior Publication Data

US 2005/0065361 A1 Mar. 24, 2005

(51) Int. Cl.$^7$ ............................................. C07C 69/96
(52) U.S. Cl. ...................... 558/280; 558/282
(58) Field of Search ................. 558/280, 282

(56) References Cited

U.S. PATENT DOCUMENTS

| | | | |
|---|---|---|---|
| 2,370,565 A | 2/1945 | Muskat et al. | |
| 2,370,566 A | 2/1945 | Muskat et al. | |
| 2,608,572 A | 8/1952 | Fischer | |
| 2,608,573 A | 8/1952 | Fischer | |
| 2,708,617 A | 5/1955 | Magat et al. | |
| 3,488,342 A | 1/1970 | Sheppard et al. | |
| 4,484,001 A | 11/1984 | Krogh | |
| 4,500,726 A | 2/1985 | Krogh | |
| 5,846,942 A | * 12/1998 | Horwell et al. | ................ 514/18 |
| 6,696,590 B2 | * 2/2004 | Bonnard et al. | ............. 558/280 |

OTHER PUBLICATIONS

Eckert et al, Angewandte Chemie, International Edition in English, Triphosgene, a Crystalline Phosgene Substitute, 1987, pp. 894–895.*

* cited by examiner

*Primary Examiner*—Paul A. Zucker
(74) *Attorney, Agent, or Firm*—Nixon & Vanderhye P.C.

(57) ABSTRACT

Alky/aryl chloroformates are prepared directly from alcohols and triphosgene. This method is simple, mild and efficient avoids use of hazardous phosgene. It can be used for the preparation of various aryl as well as alkyl chloroformates in excellent yields.

9 Claims, No Drawings

PROCESS FOR PREPARING ALKYL/ARYL CHLOROFORMATES

FIELD OF THE INVENTION

The present invention relates to a process for preparing alkyl/aryl chloroformates. More particularly, the present invention relates to a process for preparing compounds of formula R—OCOCl wherein R is selected from linear or branched alkyl, cycloalkyl, arylalkyl, aryl or substituted aryl. The present invention also provides a process for preparing alkyl/aryl chloroformates of formula R—OCOCl from triphosgene and alcohols of formula R—OH wherein R is selected from linear or branched alkyl, cycloalkyl, arylalkyl, aryl or substituted aryl in the presence of a base.

BACKGROUND OF THE INVENTION

Alkyl/aryl chloroformates of formula R—OCOCl prepared according to the process of the present invention are valuable synthetic intermediates for pesticides, perfumes, dyes, drugs, polymers and other chemicals. Carbonates prepared from chloroformates are used as solvents. Carbamates prepared from chloroformates are used in pharmaceuticals, pesticides and insecticides. Ethyl chloroformate is used in the manufacture of ore floatation agents by reaction with various xanthates [A. H. Fischer, U.S. Pat. Nos. 2,608,572 and 2,608,573 (1952)]. Chloroformates are also used in the preparation of polyurethanes [E. E. Magat, D. R. Strachan, U.S. Pat. No. 2,708,617 (1955)]. They are also used in the manufacture of optical lenses [I. E. Muskat and F. Strain, U.S. Pat. Nos. 2,370,565 and 2,370,566 (1945)]. Chloroformates are used as blowing agents for producing foam rubber [C. S. Sheppard, H. P. van Leeuwen and O. L. Mageli, U.S. Pat. No. 3,488,342 (1970)]. Some chloroformates are also used as blocking agents for aminoacids [J. A. Krogh, U.S. Pat. No. 4,484,001 (1984) and U.S. Pat. No. 4,500,726 (1985)]. They are also used for the synthesis of many heterocyclic compounds [(a) M. Matzner, R. P. Kurkjy, R. J. Cotter, Chem. Rev. 1964, 64, 645. (b) Kirk-Othmer Encyclopaedia of Chemical Technology, 4$^{th}$, Ed. Interscience, John Wiley and Sons Inc., New York, 1991, 5, 77].

In the prior art chloroformates of formula (II) are prepared by reaction of alcohols with phosgene at or below room temperature in the presence of tertiary amines [(a) D. N. Kevill In Patai, S. *The Chemistry of Acyl Halides*; Interscience, John Wiley and Sons Inc. New York, 1972; pp. 381–453. (b) Phosgene Booklet, Chemetron Chemicals, Organic Chemical Department, 386, Park Avenue South, New York, 1963. (c) Hpuben-weyl, *Methoden der Organischen Chemie*, Vol. 8, Georg Thieme Verlag, stuttgard, 1952, pp 102–105. (d) H. E. Carter, R. L. Frank and H. W. Johnston, *Organic Synthesis Col.* Vol. 3, 1955, 167]. Aryl chloroformates are synthesized from less reactive phenols at temperature above 75° C. or more readily, by first converting the phenols to an alkali metal phenoxides and reacting with phosgene in the presence of an organic solvent [(a) E. L. Wittbecker, P. W. Margan, *J. Polymer Sci*, 1959, 40, 367. (b) M. J. zabik, R. D. schuetz *J. Org. chem.* 1967, 32, 300].

Prior art also teaches the preparation of chloroformates from triphosgene using pyridine as a base [(a) Q. Wang, R. Huang, *Tetrahedron Lett.* 2001, 42, 8881. (b) P. E. Maligres, K. C. Nicolau, W. Wrasidio *Bioorg. Med. Chem. Lett.* 1993, 3, 1051. (c) D. C. Horwell, J. Hughes, J. Hunter, M. C. Pritchard, R. S. Richardson, E. Roberts, G. N. Woodruff *J. Med. Chem.*, 1991, 34, 404] and tertiary amines as base [H. Eckert, B. Forster, *Angew. Chem. Int. Ed. Engl.*, 1987, 26, 894]. Hydroquinone is also used in the preparation of chloroformates from triphosgene [G. Van den Mooter, C. Samyn, R. Kinget *Int. J. Pharm.*, 1993, 97, 133]. In most of the cases the yields of the product are not given in the reports.

The drawbacks of the above methods are low yields of the product and the starting material, phosgene, is highly toxic and hazardous for handling.

OBJECTS OF THE INVENTION

The main object of the present invention is to provide an alternate process for the preparation of chloroformates of formula R—OCOCl, which avoids the use of hazardous reagents.

Another object of the present invention is to provide a simple process for alky/arylchloroformatesof formula R—OCOCl, with improved yields.

BRIEF SUMMARY OF THE INVENTION

Accordingly, the present invention provides a process for preparing alkyl/aryl chloroformates of formula R—OCOCl wherein R is selected from the group consisting of linear alkyl, branched alkyl, cycloalkyl, arylalkyl, aryl and substituted aryl, the process comprising adding a solution of alcohol of formula R—OH wherein R is selected from the group consisting of linear alkyl, branched alkyl, cycloalkyl, arylalkyl, aryl and substituted aryl, in an organic solvent, to a mixture of triphosgene, a catalyst, a base and an organic solvent, at a temperature in the range of 0° C. to ambient for a time period in the range of 1 to 48 hours to obtain a solid, separating the solid by filtration and removing the solvent from filtrate to obtain the alkyl/aryl chloroformate formula R—OCOCl, and purifying the alkyl/aryl chloroformate.

In one embodiment of the invention the catalyst is selected from the group consisting of an organic tertiary amine and an organic amide.

In another embodiment of the invention, the organic tertiary amine comprises triethylamine.

In another embodiment of the invention, the organic amide comprises dimethyl formamide.

In another embodiment of the invention, the base is selected from the group consisting of inorganic metal carbonate and bicarbonate.

In a further embodiment of the invention, the inorganic metal carbonate is selected from the group consisting of sodium carbonate, potassium carbonate and calcium carbonate.

In a further embodiment of the invention, the bicarbonate is selected from the group consisting of sodium bicarbonate and potassium bicarbonate.

In another embodiment of the invention, the alcohol is selected from the group consisting of benzyl alcohol, n-octanol, 2-ethylcyclohexan-1-ol, n-butanol and phenol.

In yet another embodiment of the invention, the organic solvent is selected from the group consisting of acetone, acetonitrile, tetrahydrofuran, hydrocarbons selected from hexane, cyclohexane, benzene, toluene, xylene, chlorinated hydrocarbons selected from dichloromethane, dichloroethane, and preferably toluene or hexane.

In another embodiment of the invention, the solvent for the process and the solvent for the alcohol are the same.

DETAILED DESCRIPTION OF EXEMPLARY EMBODIMENTS OF

The present invention provides a process for preparing alkyl/aryl chloroformates of formula R—OCOCl where R may be linear or branched alkyl, cycloalkyl, arylalkyl, aryl and substituted aryl. The process comprises adding a solution of alcohol of formula R—OH where R may be linear or branched alkyl, cycloalkyl, arylalkyl, aryl and substituted aryl in an organic solvent to a mixture of triphosgene, a catalyst, a base and an organic solvent. The organic solvent for forming a solution of the alcohol of formula R—OH and the solvent for the reaction itself may be identical or different. The reaction is preferably carried out at a temperature in the range of 0° C. to ambient, preferably till 25° C. and for a time period in the range of 1 to 48 hours. A solid is obtained, which is separated by filtration. The solvent is then removed from the filtrate by conventional methods to leave a residue comprising the alkyl/aryl chloroformate formula R—OCOCl. The obtained product can be purified by conventional methods.

The catalyst is preferably an organic tertiary amine such as tryiethylamine or an organic amide such as dimethyl formamide. The base is preferably an inorganic metal carbonate such as sodium carbonate, potassium carbonate and calcium carbonate or a bicarbonate such as sodium bicarbonate or potassium bicarbonate. The alcohol itself is anyalkyl or aryl alcohol as indicated above, but can be selected from the group consisting of benzyl alcohol, n-octanol, 2-ethylcyclohexan-1-ol, n-butanol and phenol.

The organic solvent is preferably selected from acetone, acetonitrile, tetrahydrofuran, hydrocarbons selected from hexane, cyclohexane, benzene, toluene, xylene, chlorinated hydrocarbons selected from dichloromethane, dichloroethane. The most preferred solvents are toluene or hexane.

The invention is described herein below with the examples, which are illustrative only and should not be construed to limit the scope of the present invention in any manner.

EXAMPLE 1

A mixture of triphosgene (1.54 gm, 5.2 mmol), sodium carbonate (1.02 gm, 10 mmol) and dimethyl formamide (0.2 gm, 0.35 mmol) as a catalyst, in toluene (20 ml) was cooled to 0° C. and stirred at this temperature for 30 min. A solution of benzyl alcohol (1.27 gm, 10 mmol) in toluene (20 ml) was added slowly over a period 30 min. The reaction mixture was stirred at 0° C. for 8 h. The GLC of the reaction mixture showed 70% conversion with 98.5% selectivity for benzyl chloroformate.

EXAMPLE 2

A mixture of triphosgene (1.54 gm, 5.2 mmol), sodium carbonate (1.02 gm, 10 mmol) and dimethyl formamide (0.2 gm, 0.35 mmol) as a catalyst, in toluene (20 ml) was cooled to 0° C. and stirred at this temperature for 30 min. A solution of n-octanol (1.30 gm, 10 mmol) in toluene (20 ml) was added slowly over a period 30 min. The reaction mixture was stirred at 0° C. for 8 h. The GLC of the reaction mixture showed 93% conversion with 100% selectivity for n-octyl chloroformate. The solid sodium carbonate was removed by filtration and the solvent from the filtrate was removed under reduced pressure to get colourless oil (1.88 gm, 98% yield).

EXAMPLE 3

A mixture of triphosgene (1.54 gm, 5.2 mmol), sodium carbonate (1.02 gm, 10 mmol) and dimethyl formamide (0.2 gm, 0.35 mmol) as a catalyst, in toluene (20 ml) was cooled to 0° C. and stirred at this temperature for 30 min. A solution of 2-ethylcyclohexan-1-ol (1.30 gm, 10 mmol) in toluene (20 ml) was added slowly over a period 30 min. The reaction mixture was stirred at 0° C. for 8 h. The GLC of the reaction mixture showed 94% conversion with 100% selectivity for [(2-ethylcyclohexan-1-ol)yl] chloroformate. The solid sodium carbonate was removed by filtration and the solvent from the filtrate was removed under reduced pressure to get colourless oil (1.84 gm, 96% yield).

EXAMPLE 4

A mixture of triphosgene (1.54 gm, 5.2 mmol), sodium carbonate (1.02 gm, 10 mmol) and dimethyl formamide (0.2 gm, 0.35 mmol) as a catalyst, in toluene (20 ml) was cooled to 0° C. and stirred at this temperature for 30 min. A solution of n-butanol (0.75 gm, 10 mmol) in toluene (20 ml) was added slowly over a period 30 min. The reaction mixture was stirred at 0° C. for 8 h. The GLC of the reaction mixture showed 94% conversion with 100% selectivity for n-butyl chloroformate. The solid sodium carbonate was removed by filtration and the solvent from the filtrate was removed under reduced pressure to get colourless oil (1.31 gm, 96% yield).

EXAMPLE 5

A mixture of triphosgene (1.54 gm, 5.2 mmol), sodium carbonate (1.02 gm, 10 mmol) and dimethyl formamide (0.2 gm, 0.35 mmol) as a catalyst, in toluene (20 ml) was cooled to 0° C. and stirred at this temperature for 30 min. A solution of phenol (0.94 gm, 10 mmol) in toluene (20 ml) was added slowly over a period 30 min. The reaction mixture was stirred at 0° C. for 8 h. The GLC of the reaction mixture showed 60% conversion with 90% selectivity for phenyl chloroformate. The solid sodium carbonate was removed by filtration and the solvent from the filtrate was removed under reduced pressure to get colourless oil (1.03 gm, 66% yield).

EXAMPLE 6

A mixture of triphosgene (1.54 gm, 5.2 mmol), sodium carbonate (1.02 gm, 10 mmol) and dimethyl formamide (0.2 gm, 0.35 mmol) as a catalyst, in toluene (20 ml) was cooled to 0° C. and stirred at this temperature for 30 min. A solution of n-octanol (1.30 gm, 10 mmol) in toluene (20 ml) was added slowly over a period 30 min. The reaction mixture was stirred at room temperature for 8 h. The GLC of the reaction mixture showed 85% conversion with 100% selectivity for n-octyl chloroformate. The solid sodium carbonate was removed by filtration and the solvent from the filtrate was removed under reduced pressure to get colourless oil (1.72 gm, 90% yield).

EXAMPLE 7

A mixture of triphosgene (1.54 gm, 5.2 mmol), sodium carbonate (1.02 gm, 10 mmol) and triethylamine (0.35 gm, 0.35 mmol), in toluene (20 ml) was cooled to 0° C. and stirred at this temperature for 30 min. A solution of n-octanol (1.30 gm, 10 mmol) in toluene (20 ml) was added slowly over a period 30 min. The reaction mixture was stirred at 0° C. for 8 h. The GLC of the reaction mixture showed 93% conversion with 100% selectivity for n-octyl chloroformate. The solid sodium carbonate was removed by filtration and the solvent from the filtrate was removed under reduced pressure to get colourless oil (1.85 gm, 96% yield).

EXAMPLE 8

A mixture of triphosgene (1.54 gm, 5.2 mmol), potassium carbonate (1.38 gm, 10 mmol) and dimethyl formamide (0.2 gm, 0.35 mmol) as a catalyst, in toluene (20 ml) was cooled to 0° C. and stirred at this temperature for 30 min. A solution of benzyl alcohol (1.27 gm, 10 mmol) in toluene (20 ml) was added slowly over a period 30 min. The reaction mixture was stirred at 0° C. for 8 h. The GLC of the reaction mixture showed 79% conversion with 98.5% selectivity for benzyl chloroformate.

EXAMPLE 9

A mixture of triphosgene (1.54 gm, 5.2 mmol), sodium bicarbonate (0.84 gm, 10 mmol) and dimethyl formamide (0.2 gm, 0.35 mmol) as a catalyst, in toluene (20 ml) was cooled to 0° C. and stirred at this temperature for 30 min. A solution of benzyl alcohol (1.27 gm, 10 mmol) in toluene (20 ml) was added slowly over a period 30 min. The reaction mixture was stirred at 0° C. for 8 h. The GLC of the reaction mixture showed 77% conversion with 98% selectivity for benzyl chloroformate.

ADVANTAGES OF THE INVENTION

1. The present invention provides an alternate process for the preparation of chloroformates of formula R—OCOCl, which avoids the use of hazardous reagents.
2. Another advantage of the invention is that the process is simple and also results in alky/arylchloroformates of formula R—OCOCl with improved yields.

What is claimed is:

1. A process for preparing alkyl/aryl chloroformates of formula R—OCOCl wherein R is selected from the group consisting of linear alkyl, branched alkyl, cycloalkyl, arylalkyl, aryl and substituted aryl, the process comprising:
    adding a solution of alcohol of formula R—OH wherein R is selected from the group consisting of linear alkyl, branched alkyl, cycloalkyl, arylalkyl, aryl and substituted aryl, in an organic solvent, to a mixture of triphosgene, a catalyst, a base and an organic solvent, at a temperature in the range of 0° C. to ambient for a time period in the range of 1 to 48 hours to obtain a solid wherein the base is selected from the group consisting of inorganic metal-carbonate and bicarbonate,
    separating the solid by filtration and removing the solvent from filtrate to obtain the alkyl/aryl chloroformate formula R—OCOCl, and
    purifying the alkyl/aryl chloroformate.

2. A process as in claim 1 wherein the catalyst is selected from the group consisting of an organic tertiary amine and an organic amide.

3. A process as in claim 1 wherein the catalyst comprises triethylamine.

4. A process as in claim 1 wherein the catalyst comprises dimethyl formamide.

5. A process as in claim 1 wherein the inorganic metal carbonate is selected from the group consisting of sodium carbonate, potassium carbonate and calcium carbonate.

6. A process as in claim 1 wherein the bicarbonate is selected from the group consisting of sodium bicarbonate and potassium bicarbonate.

7. A process as in claim 1 wherein the alcohol is selected from the group consisting of benzyl alcohol, n-octanol, 2-ethylcyclohexan-1-ol, n-butanol and phenol.

8. A process as claim 1 wherein the organic solvent is selected from the group consisting of acetone, acetonitrile, tetrahydrofuran, hydrocarbons selected from hexane, cylohexane, benzene, toluene, xylene, chlorinated hydrocarbons selected from dichloromethane, dichloroethane, and preferably toluene or hexane.

9. A process as in claim 1 wherein the solvent for the process and the solvent for the alcohol are the same.

* * * * *